(12) United States Patent
Lutz

(10) Patent No.: US 11,406,581 B2
(45) Date of Patent: Aug. 9, 2022

(54) PROTECTANTS

(71) Applicant: Lincoln Manufacturing Inc., Lincoln, RI (US)

(72) Inventor: Patrick Jay Lutz, Nazareth, PA (US)

(73) Assignee: BARENTZ NORTH AMERICA, LLC, Avon, OH (US)

( * ) Notice: Subject to any disclaimer, the term of this patent is extended or adjusted under 35 U.S.C. 154(b) by 0 days.

(21) Appl. No.: 16/411,692

(22) Filed: May 14, 2019

(65) Prior Publication Data

US 2019/0343749 A1 Nov. 14, 2019

Related U.S. Application Data

(60) Provisional application No. 62/671,279, filed on May 14, 2018.

(51) Int. Cl.
| | | |
|---|---|---|
| *A61K 8/49* | (2006.01) | |
| *A61K 8/368* | (2006.01) | |
| *A61Q 5/02* | (2006.01) | |
| *A61Q 19/10* | (2006.01) | |
| *A61Q 17/00* | (2006.01) | |

(52) U.S. Cl.
CPC ............ *A61K 8/4926* (2013.01); *A61K 8/368* (2013.01); *A61Q 5/02* (2013.01); *A61Q 17/005* (2013.01); *A61Q 19/10* (2013.01); *A61K 2800/30* (2013.01); *A61K 2800/5922* (2013.01); *A61K 2800/74* (2013.01)

(58) Field of Classification Search
None
See application file for complete search history.

(56) References Cited

U.S. PATENT DOCUMENTS

| | | | | |
|---|---|---|---|---|
| 8,969,390 B2 * | 3/2015 | Klug | ...................... | A61K 8/368 |
| | | | | 514/345 |
| 2019/0224099 A1 * | 7/2019 | Gauczinski | .......... | A61K 8/4973 |
| 2019/0350200 A1 * | 11/2019 | Sharma | .................. | A01N 43/40 |

FOREIGN PATENT DOCUMENTS

WO   WO-2013006917 A1   1/2013

* cited by examiner

*Primary Examiner* — Nannette Holloman
(74) *Attorney, Agent, or Firm* — Blank Rome LLP

(57) ABSTRACT

The present invention relates to the use of natural protectants comprising (i) a cetylpyridinium salt (such as cetylpyridinium chloride) or p-anisic acid or a salt thereof (such as sodium p-anisate) and (ii) piroctone olamine to prevent microbial growth in a product, such as a personal care product.

16 Claims, No Drawings

PROTECTANTS

This application claims the benefit of U.S. Provisional Application No. 62/671,279, filed May 14, 2018, which is hereby incorporated by reference.

FIELD OF THE INVENTION

The present invention relates to the use of protectants comprising (i) a cetylpyridinium salt (such as cetylpyridinium chloride) or p-anisic acid or a salt thereof (such as sodium p-anisate), and (ii) piroctone olamine to prevent microbial growth and preserve a product.

BACKGROUND

EP 2731634 discloses a disinfecting formulation comprising alcohol including ethanol; an essential oil comprising cineole, in particular eucalyptus oil; an emollient including glycerin; and other ingredients comprising piroctone olamine, acrylic acid based polymer and 2-amino-2-methyl-1-propanol.

There is a continuing need for low cost and safe preservative systems which are effective against a broad spectrum of microorganisms.

SUMMARY OF THE INVENTION

The protectants of the present invention are relatively cheap to make and easy to work with and incorporate into finished products. In one embodiment, the protectant comprises (i) a cetylpyridinium salt (such as cetylpyridinium chloride) or p-anisic acid or a salt thereof (such as sodium p-anisate) and (ii) piroctone olamine. In one preferred embodiment, the protectant comprises a synergistic amount of (i) cetylpyridinium salt (such as cetylpyridinium chloride) or p-anisic acid or a salt thereof (such as sodium p-anisate) and (ii) piroctone olamine. In another preferred embodiment, the protectant comprises a synergistic amount of (i) cetylpyridinium chloride and (ii) piroctone olamine to inhibit microbial growth (e.g., bacterial and/or fungi growth). In yet another preferred embodiment, the protectant comprises a synergistic amount of (i) sodium p-anisate and (ii) piroctone olamine to inhibit microbial growth (e.g., bacterial and/or fungi growth).

The protectant optionally further comprises (i) one or more natural or naturally derived compounds and/or (ii) one or more other antimicrobials.

One embodiment is a product comprising a sufficient amount of (i) a cetylpyridinium salt (such as cetylpyridinium chloride) or p-anisic acid or a salt thereof (such as sodium p-anisate) and (ii) piroctone olamine to inhibit microbial growth (e.g., bacterial and/or fungi growth) in the product. In one embodiment, the product is not intended for oral administration to an animal. The protectant of the present invention is particularly effective for personal care products, such as a shampoo.

Another embodiment is a method of killing and/or inhibiting the growth of microorganisms (e.g., fungi and/or bacteria) on a substrate by applying an effective amount of (i) a cetylpyridinium salt (such as cetylpyridinium chloride) or p-anisic acid or a salt thereof (such as sodium p-anisate) and (ii) piroctone olamine to the substrate.

DETAILED DESCRIPTION OF THE INVENTION

Definitions

The term "microorganisms" includes, but is not limited to, bacteria, fungi, yeasts, algae, insects, and pests.

The term "personal care products" refers to products intended for application to the human body, such as to skin, hair, and nails, including, but not limited to, shampoos, conditioners, creams, lotions (such as body lotions), cosmetics, and soaps.

Protectant

In one embodiment, the protectant includes a cetylpyridinium salt, such as cetylpyridinium chloride, and piroctone olamine. In a preferred embodiment, the protectant includes cetylpyridinium chloride and piroctone olamine. In one preferred embodiment, the protectant comprises a sufficient amount of cetylpyridinium salt (such as cetylpyridinium chloride) and piroctone olamine to inhibit microbial growth (such as bacterial and/or fungal growth) in the product.

Preferably, the protectant includes a synergistic amount (for example, for inhibiting growth of microorganisms, such as bacteria and/or fungi) of a cetylpyridinium salt, such as cetylpyridinium chloride, and piroctone olamine.

In one embodiment, the weight ratio of (i) cetylpyridinium salt (such as cetylpyridinium chloride) to (ii) piroctone olamine may range from about 0.01:100 to about 100:0.01, such as from about 0.1:20 to about 20:0.1, from about 1:10 to about 10:1, from about 5:1 to about 1:5. In another embodiment, the weight ratio ranges from about 1:1 to about 10:1, such as from about 2:1 to about 8:1 or from about 3:1 to about 7:1 (e.g., 5:1).

In another embodiment, the product contains (i) from about 0.001 to about 10% by weight of cetylpyridinium salt (such as cetylpyridinium chloride), such as from about 0.001 to about 4%, from about 0.01 to about 2%, from about 0.05 to about 2%, from about 0.1 to about 1%, or from about 0.1 to about 0.5% by weight of cetylpyridinium salt, based upon 100% total weight of product, and (ii) from about 0.001 to about 10% by weight of piroctone olamine, such as from about 0.001 to about 4%, from about 0.01 to about 2%, from about 0.01 to about 1%, from about 0.01 to about 0.1%, from about 0.02 to about 0.08%, or from about 0.03 to about 0.07% by weight of piroctone olamine, based upon 100% total weight of product.

In yet another embodiment, the protectant includes p-anisic acid or a salt thereof (such as sodium p-anisate) and piroctone olamine. In a preferred embodiment, the protectant includes sodium p-anisate and piroctone olamine. In one preferred embodiment, the protectant comprises a sufficient amount of p-anisic acid or a salt thereof (such as sodium p-anisate) and piroctone olamine to inhibit microbial growth (such as bacterial and/or fungal growth) in the product.

Preferably, the protectant includes a synergistic amount (for example, for inhibiting growth of microorganisms, such as bacteria and/or fungi) of p-anisic acid or a salt thereof (such as sodium p-anisate) and piroctone olamine.

In one embodiment, the weight ratio of (i) p-anisic acid or a salt thereof (such as sodium p-anisate) to (ii) piroctone olamine may range from about 0.01:100 to about 100:0.01, such as from about 0.1:20 to about 20:0.1, from about 1:1 to about 20:1, from about 15:1 to about 1:1. In another embodiment, the weight ratio ranges from about 15:1 to about 2:1, such as from about 15:1 to about 5:1 (e.g., 10:1) or from about 8:1 to about 3:1.

In another embodiment, the product contains (i) from about 0.001 to about 10% by weight of p-anisic acid or a salt thereof (such as sodium p-anisate), such as from about 0.01 to about 5%, from about 0.01 to about 2%, from about 0.05 to about 2%, from about 0.1 to about 1%, or from about 0.2 to about 0.8% by weight of p-anisic acid or a salt thereof (such as sodium p-anisate), based upon 100% total weight of product, and (ii) from about 0.001 to about 10% by weight of piroctone olamine, such as from about 0.001 to about 4%, from about 0.01 to about 2%, from about 0.01 to about 1%, from about 0.01 to about 0.1%, from about 0.02 to about 0.08%, or from about 0.03 to about 0.07% by weight of piroctone olamine, based upon 100% total weight of product.

In yet another embodiment, the product contains a sufficient amount of (i) cetylpyridinium salt (such as cetylpyridinium chloride) or p-anisic acid or a salt thereof (such as sodium p-anisate) and (ii) piroctone olamine in combination with one or more natural and/or naturally derived compounds and/or other antimicrobials (such as one or more synthetic antimicrobials) to inhibit microbial growth in the product.

Natural and Naturally Derived Compounds and Other Antimicrobials

The product may further contain (i) one or more natural or naturally derived compounds and/or (ii) one or more other antimicrobials (such as one or more synthetic antimicrobials), for example, to aid in inhibiting microbial growth in the product.

Suitable natural or naturally derived compounds include, but are not limited to, 1,3 propanediol (only all natural type), glycereth-2 cocoate, benzyl alcohol (naturally derived from cassia), glycerin, organic solvents (e.g., ethylhexyl glycerin, phenoxyethanol, caprylyl glycols, pentylene glycol (natural), phenethyl alcohol (natural), and hexylene glycol), organic acids (e.g., sorbic acid, benzoic acid, and citric acid), and any combination of any of the foregoing.

Products

The products described above may be a solid or liquid. In a preferred embodiment, the products described herein are substantially free or completely free of parabens (such as methylparaben, ethylparaben, and propylparaben), formaldehyde donors, and/or isothiazolinones. According to one embodiment, the product contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of parabens, formaldehyde donors, and/or isothiazolinones, based upon 100% total weight of product. According to one embodiment, the product does not contain a preservative effective amount of a preservative. According to yet another embodiment, the product is all natural.

In another embodiment, the product is substantially free or completely free of synthetic preservatives. According to one embodiment, the product contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of synthetic preservatives, based upon 100% total weight of product.

In one embodiment, the product (for example, a shampoo) has a pH below about 8.

In one embodiment, the product is not intended for oral administration to an animal (e.g., a human subject). In another embodiment, the product is other than a foodstuff, pharmaceutical, cosmetic, or nutritional supplement. For example, the product can be a household (e.g., personal care), industrial, or institutional product. In one preferred embodiment, the product is a personal care product, such as a shampoo, body lotion, conditioner, or soap.

The (i) cetylpyridinium salt (such as cetylpyridinium chloride) or p-anisic acid or a salt thereof (such as sodium p-anisate) and (ii) piroctone olamine optionally in combination with one or more natural or naturally derived compounds and/or other antimicrobials may be incorporated into substrates susceptible to microbial growth as a protectant to inhibit microbial growth. Suitable substrates include, but are not limited to, a personal care product, such as a shampoo, conditioner, cream, lotion (such as body lotion), cosmetic, or soap; a household product, such as a fabric softener, laundry detergent, or hard surface cleaner; or an industrial product, such as paint, coatings, wood, textile, adhesive, sealant, leather, rope, paper, pulp, paper board, sheet rock, ceiling tiles, plastic, fuel, petroleum, oil, rubber working fluid, metal working fluid, starches (such as pet food starch), or mineral slurry, such as a slurry of clay, calcium carbonate, or titanium oxide ($TiO_2$).

Generally, (i) the cetylpyridinium salt (such as cetylpyridinium chloride) or p-anisic acid or a salt thereof (such as sodium p-anisate) and (ii) piroctone olamine alone or in combination with the one or more natural or naturally derived compounds and/or other antimicrobials acts quickly (e.g., reduces the microorganism (e.g., bacteria and/or fungi) count by 95, 99, 99.9, or 99.99% typically within an hour) and maintains efficacy (e.g., maintains less than 1,000 or 100 cfu/g) over long periods of time (e.g., for at least 7, 10, 14, or 28 days).

The protectant containing (i) the cetylpyridinium salt (such as cetylpyridinium chloride) or p-anisic acid or a salt thereof (such as sodium p-anisate) and (ii) piroctone olamine with or without the one or more natural or naturally derived compounds and/or other antimicrobials may include a solvent, such as water and water miscible solvents, including, but not limited to, alcohols (e.g., methanol, ethanol, propanol, iso-propanol, and butanol), glycols (e.g. glycerin, diglycerin, butylene glycol, butoxydiglycol, propylene glycol, and dipropylene glycol), esters, ethers, polyethers, and any combination of any of the foregoing. For example, the solvent may comprise water and one or more glycol and/or one or more alcohol, such as glycerin, phenoxyethanol, benzyl alcohol, or ethanol. A specific solvent system comprises water and a glycol, such as glycerin. A second specific solvent system comprises water and an alcohol, such as ethanol.

The protectant may be incorporated into an aqueous or oil based system or an emulsion. A suitable solvent for an oil based system is phenoxyethanol and/or benzyl alcohol.

In one embodiment, the protectant is comprised of all natural products. The protectant can be a liquid or a solid (e.g., a powder).

To prepare a formulation containing the product of the present invention, a concentrate of the protectant may be first prepared. The concentrate may include from about 0.01 to about 100% by weight of the protectant such as from about 5 to about 80% by weight of the protectant, based upon 100% total weight of concentrate. For a two-component protectant, the concentrate broadly contains from about 0.01 to about 99.99% by weight of the cetylpyridinium salt (such as cetylpyridinium chloride) or p-anisic acid or a salt thereof (such as sodium p-anisate) and from about 99.99% to about 0.01% by weight of piroctone olamine, based upon 100% total weight of concentrate). The weight ratio of (i) the cetylpyridinium salt or p-anisic acid or a salt thereof to (ii) piroctone olamine in the concentrate may the same as described for the protectants above.

Before use, the concentrate may be diluted, such as with the same solvent as was used in the concentrate, and/or incorporated into a product. Use dilutions of the composition typically include a sufficient amount of protectant to inhibit microbial growth (e.g., fungi growth).

Generally, use dilutions contain from about 0.0001% or 0.01% to about 2% by weight of the concentrate. According to one preferred embodiment, use dilutions contain from about 0.1 to about 1% by weight of the concentrate. In more preferred embodiments, the use dilution contains 0.2, 0.25 or 0.30% by weight of the concentrate.

According to another embodiment, the protectant is incorporated into a product at a concentration of about 0.1 to about 1 or 2% by weight, based upon 100% total weight of product.

Method of Inhibiting Microbial Growth

Another embodiment of the present invention is a method for killing and/or inhibiting the growth of microorganisms, such as bacteria (e.g., *S. aureus* (ATCC #6538), *P. aeruginosa* (ATCC #9027), and *E. coli* (ATCC #8739)) and/or fungi (including plant and tree fungi) (e.g., *Candida albicans, Aspergillus niger* and *Phytophthora ramrum*), on a substrate by applying a sufficient amount of the protectant to the substrate or incorporating a sufficient amount of the protectant into the substrate. The protectant may be applied to or incorporated into the substrate by any method known in the art including, but not limited to, brushing, dipping, soaking, vacuum impregnation, and pressure treatment.

The protectant may be prepared by mixing (i) the cetylpyridinium salt (such as cetylpyridinium chloride) or p-anisic acid or a salt thereof (such as sodium p-anisate) and (ii) piroctone olamine and optionally, one or more natural or naturally derived compounds, solvents, and/or adjuvants. The mixture may be heated and/or stirred to expedite mixing.

Example 1

The CTFA Preservative Challenge Test was performed on a shampoo containing the samples below against a mixture of bacteria having an initial count of $4\times10^6$ cfu/mL. The shampoos inoculated with bacteria were allowed to stand for 7 or 14 days. The samples were evaluated for surviving organisms on day 7 or day 14 for bacteria-innoculated shampoos.

The results for cetylpyridinium chloride and piroctone olamine are shown in Table 1 below.

TABLE 1

| Sample | Mixed Bacteria Day 14 Count (cfu/mL) |
| --- | --- |
| 1% cetylpyridinium chloride | $7 \times 10^3$ (<99% kill reduction) |
| 0.1% Piroctone olamine | $1.3 \times 10^5$ (<97% kill reduction) |

TABLE 1-continued

| Sample | Mixed Bacteria Day 14 Count (cfu/mL) |
| --- | --- |
| 0.25% cetylpyridinium chloride and 0.05% piroctone olamine | <10 (>99.999% kill reduction) |

From Table 1, synergism for 0.25% cetylpyridinium chloride and 0.05% piroctone olamine against mixed bacteria in shampoo was calculated by the method described in C. E. Kull et al., "Mixtures of Quaternary Ammonium Compounds and Long-chain Fatty Acids as Antifungal Agents", Applied Microbiology, 9:538-541 (1961). The synergism value $(Q_A/Q_a+Q_B/Q_b)$ was determined. $Q_A$ and $Q_B$ are concentrations of cetylpyridinium chloride and pircotine olamine, respectively, (in percent by weight) in the mixture, which yielded 100% retardation of the bacteria, i.e., resulted in a plate count of <10 cfu/g after 14 days. $Q_a$ is the concentration of cetylpyridinium chloride alone (in percent by weight) required to yield 100% retardation of the bacteria. $Q_b$ is the concentration of pircotine olamine alone (in percent by weight) required to yield 100% retardation of the bacteria. When the value of $(Q_A/Q_a+Q_B/Q_b)$ is less than one, the mixture is synergistic. Values for $(Q_A/Q_a+Q_B/Q_b)$ of 1 and greater represent an additive effect and an antagonistic effect, respectively. Here, $(Q_A/Q_a+Q_B/Q_b)$ is $((0.05\%/>0.1\%)+(0.25\%/>1\%))$ or <0.75. Accordingly, the mixture of 0.25% cetylpyridinium chloride and 0.05% piroctone olamine is synergistic.

The results for sodium p-anisate and piroctone olamine are shown in Table 2 below.

TABLE 2

| Sample | Mixed Bacteria Day 7 Count (cfu/mL) |
| --- | --- |
| 1% sodium p-anisate | $2.3 \times 10^4$ (<99% kill reduction) |
| 0.1% Piroctone olamine | $1.2 \times 10^5$ (<97% kill reduction) |
| 0.5% sodium p-anisate and 0.05% piroctone olamine | $7.0 \times 10^3$ (>99.999% kill reduction) |

Accordingly, the mixture of 0.5% sodium p-anisate and 0.05% piroctone olamine is synergistic.

All references, patent applications, and patents cited herein are hereby incorporated by reference.

The invention claimed is:

1. A natural product consisting essentially of a sufficient amount of (i) p-anisic acid or a salt thereof and (ii) piroctone olamine to inhibit microbial growth in the product, wherein the product is substantially free of isothiazolinones and synthetic preservatives.

2. The product of claim 1, wherein the product consists essentially of a sufficient amount of sodium p-anisate and piroctone olamine to inhibit microbial growth in the product.

3. The product of claim 1, wherein the product is substantially free of parabens and formaldehyde donors.

4. The product of claim 1, wherein the product is free of parabens.

5. The product of claim 1, wherein the product consists essentially of from about 0.01 to about 2% by weight of sodium p-anisate and from about 0.01 to about 1% by weight of piroctone olamine, based upon 100% total weight of the product.

6. The product of claim 1, wherein the product consists essentially of from about 0.1 to about 1% by weight of sodium p-anisate and from about 0.01 to about 0.1% by weight of piroctone olamine, based upon 100% total weight of the product.

7. The product of claim 1, wherein the product is other than a foodstuff, pharmaceutical, cosmetic, or nutritional supplement.

8. The product of claim 1, wherein the product is a personal care product.

9. The product of claim 8, wherein the personal care product is a shampoo, body lotion, conditioner, or soap.

10. A method of killing and/or inhibiting the growth of microorganisms on a substrate comprising applying an effective amount of the product of claim 2 to the substrate.

11. A method of killing and/or inhibiting the growth of microorganisms on a substrate comprising applying an effective amount of a product of claim 1 to the substrate.

12. The method of claim 11, wherein the microorganisms are selected from *S. aureus, P. aeruginosa, E. coli, Candida albicans, Aspergillus niger* and *Phytophthora ramrum*.

13. A product consisting of (i) p-anisic acid or a salt thereof, (ii) piroctone olamine, and (iii) optionally, water.

14. The product of claim 13, wherein the product consists of (i) p-anisic acid or a salt thereof and (ii) piroctone olamine.

15. The product of claim 1, wherein the weight ratio of p-anisic acid or a salt thereof to piroctone olamine is about 15:1 to about 5:1.

16. The product of claim 2, wherein the weight ratio of sodium p-anisate to piroctone olamine is about 15:1 to about 5:1.

* * * * *